(12) United States Patent
Font Ventura et al.

(10) Patent No.: US 11,167,088 B2
(45) Date of Patent: Nov. 9, 2021

(54) DEVICE FOR ADMINISTERING MEDICINAL PRODUCTS

(71) Applicant: HIPRA SCIENTIFIC, S.L.U., Amer (ES)

(72) Inventors: Marc Font Ventura, Cerviá De Ter (ES); Maria Glòria Pujol Prat, Anglès (ES); Joan Carles Pons Moll, Girona (ES)

(73) Assignee: HIPRA SCIENTIFIC, S.L.U., Amer (ES)

( * ) Notice: Subject to any disclaimer, the term of this patent is extended or adjusted under 35 U.S.C. 154(b) by 423 days.

(21) Appl. No.: 15/536,120

(22) PCT Filed: Dec. 22, 2015

(86) PCT No.: PCT/EP2015/081079
§ 371 (c)(1),
(2) Date: Jun. 14, 2017

(87) PCT Pub. No.: WO2016/102619
PCT Pub. Date: Jun. 30, 2016

(65) Prior Publication Data
US 2017/0361020 A1 Dec. 21, 2017

(30) Foreign Application Priority Data

Dec. 23, 2014 (EP) .................................... 14200035

(51) Int. Cl.
*A61M 5/30* (2006.01)
*A61M 5/315* (2006.01)

(52) U.S. Cl.
CPC .......... *A61M 5/30* (2013.01); *A61M 5/31541* (2013.01); *A61M 2205/00* (2013.01);
(Continued)

(58) Field of Classification Search
CPC .......... A61M 2205/60; A61M 5/16845; A61M 5/1684; A61M 5/16804; A61M 5/30;
(Continued)

(56) References Cited

U.S. PATENT DOCUMENTS

| | | | |
|---|---|---|---|
| 6,425,879 B1* | 7/2002 | Egger | ..................... A61M 5/30 604/67 |
| 6,523,752 B2* | 2/2003 | Nishitani | ................ B07C 7/005 235/375 |

(Continued)

FOREIGN PATENT DOCUMENTS

| | | |
|---|---|---|
| EP | 1515763 A1 | 3/2005 |
| EP | 2756855 A1 | 7/2014 |

(Continued)

OTHER PUBLICATIONS

International Search Report and Written Opinion for Application No. PCT/EP2015/081079 dated Mar. 21, 2016, 12 pages.

(Continued)

*Primary Examiner* — Nilay J Shah
(74) *Attorney, Agent, or Firm* — Squire Patton Boggs (US) LLP

(57) ABSTRACT

An injection device includes a container receiving receptacle configured for receiving a container for containing a medicinal product to be administered; a dispensing mechanism for causing the product in the container to be injected; and a RFID system associated with the container receiving receptacle capable of communicating bidirectionally with a RFID tag attached to the container and enabling the administration of the product only under given conditions. The RFID tag can be therefore read and written by the RFID system. The RFID system further includes an antenna arranged at least partially covering the RFID tag. The dispensing mechanism is triggered by a contact sensor when the device is pressed onto the animal's skin. The needle-free injection device is (Continued)

capable of communicating with external devices (PC, laptops, tablets, smartphones and the like).

19 Claims, 2 Drawing Sheets

(52) U.S. Cl.
CPC ............ *A61M 2205/215* (2013.01); *A61M 2205/3576* (2013.01); *A61M 2205/3584* (2013.01); *A61M 2205/3592* (2013.01); *A61M 2250/00* (2013.01)

(58) Field of Classification Search
CPC ......... A61M 5/31541; A61M 2205/00; A61M 2205/215; A61M 2205/3576; A61M 2205/3584; A61M 2205/3592; A61M 2005/2013; A61M 2005/208; A61M 2005/3114; A61M 2005/3115; A61M 5/2033; A61M 5/3007
See application file for complete search history.

(56) References Cited

U.S. PATENT DOCUMENTS

| | | | | |
|---|---|---|---|---|
| 9,744,300 B2* | 8/2017 | Kamen | ............... | A61M 5/172 |
| 9,925,333 B2* | 3/2018 | Hooven | ............... | A61M 5/152 |
| 2003/0183226 A1* | 10/2003 | Brand | ............ | A61M 15/0065 128/200.23 |
| 2008/0191013 A1 | 8/2008 | Liberatore | | |
| 2009/0156931 A1* | 6/2009 | Nemoto | ............ | A61M 5/14546 600/432 |
| 2010/0056909 A1* | 3/2010 | Fago | ................ | A61M 5/007 600/432 |
| 2011/0118694 A1* | 5/2011 | Yodfat | ............... | G06F 19/3468 604/500 |
| 2013/0085443 A1* | 4/2013 | Lowery | ............... | G05D 7/0635 604/65 |
| 2013/0248601 A1 | 9/2013 | Liang et al. | | |
| 2014/0276535 A1 | 9/2014 | Wood et al. | | |

FOREIGN PATENT DOCUMENTS

| | | |
|---|---|---|
| RU | 2447905 C2 | 4/2012 |
| WO | WO 2003/103751 A1 | 12/2003 |
| WO | WO 2010/021953 A2 | 2/2010 |
| WO | WO 2012/048268 A2 | 4/2012 |
| WO | WO 2014/107766 A1 | 7/2014 |

OTHER PUBLICATIONS

Mitragotri et al. "Current status and future prospects of needle-free liquid jet injectors," Nat Rev Drug Discov., 2006, vol. 5, pp. 543-548.

Decision to Grant a Patent for Invention dated Oct. 1, 2019 corresponding to Russian Patent Application No. 2017120534/14(035607), and English translation thereof.

* cited by examiner

DEVICE FOR ADMINISTERING MEDICINAL PRODUCTS

This application claims the benefit of European Patent Application EP14200035.5 filed Dec. 23, 2014.

TECHNICAL FIELD

The present disclosure relates to devices for administering medicinal products such as fluid formulations or compositions containing a medicinal substance or product. It specifically relates to a needle-free injection device for administering medicinal products such as drugs, e.g. vaccines and the like, to animals.

The present disclosure also relates to systems for managing the administration of medicinal products. It specifically relates to a system for managing the administration of medicinal products comprising said needle-free injection device.

BACKGROUND

Needle-free injection devices are known in the art for administering medicinal products to animals and humans. Instead of using a hypodermic needle, the needle-free injection devices make use of a narrow jet of a high-pressure fluid that is injected through the skin.

One typical application example of the needle-free injection devices is mass vaccinations in animals. The needle-free injection devices is capable of delivering a target molecule at a variety of tissue depths ranging from the dermis to the muscle, depending on the force generated by the injector (Mitragotri S., Nat Rev Drug Discov. 2006; 5:543-548; Schramm-Baxter J., et al., J. Control Release, 2004; 97:527-535).

Known needle-free injection devices comprise a housing inside of which a chamber if formed for containing a medicinal product to be injected through a dispensing outlet out of the chamber. A dispensing mechanism is also provided for performing the injection of the medicinal product.

Although said needle-free injection devices are complex as compared to needle-and-syringe equipment, they have significant advantages. For example, it has been found that transmission of diseases between animals is reduced and mass vaccination is less time consuming and more accurate.

One example of a needle-free injection device is disclosed in document EP1515763. The needle-free injection device disclosed in this document comprises a chamber adapted for containing a product to be injected out of the chamber through a discharge nozzle. The chamber is connected through a supply line to a reservoir containing the product to be injected. The device includes a dispensing mechanism comprising a powered cam adapted for displacing a piston that is arranged in the chamber against a spring. Displacement of the piston causes the product to be injected out of the chamber. Operation of said dispensing mechanism is dependent on a sensor such as a LED provided over the supply line. The sensor is suitable for detecting the presence of the product to be injected.

The provision of a sensor in the above needle-free injection device has the advantage that it allows a safe product administration process. The dispensing mechanism does not move the piston when then sensor fails to detect the presence of product to be injected, so the product is not injected. However, such injection device does not provide product traceability so product administration processes should be controlled manually by the operator. This results in a time consuming and tedious task.

In addition, the needle-free injection device disclosed in EP1515763 is only capable of discriminating between a product to be injected, such as a vaccine, and a cleaning solution. This needle-free injection device is not capable of distinguishing what type of product, e.g. a vaccine, is actually being administered to an animal.

Therefore, there is a need to provide a needle-free injection device capable of facilitating veterinary safe practices on the one hand, and capable of providing product traceability on the other hand.

SUMMARY

A needle-free injection device for administering a medicinal product to an animal is disclosed herein.

The present needle-free injection device comprises a container receiving receptacle which may be formed, for example, within a housing. The container receiving receptacle is configured for receiving a container for containing a medicinal product to be administered.

As used herein, a medicinal substance or product refers to any substance or combination of substances that can be used to prevent or treat a disorder, including diseases, i.e., to aid in preventing, ameliorating, treating or curing the disorder. Such a substance may for example be a chemical, pharmaceutical or biological compound, such as a natural or synthetic peptide or protein, a (poly-)saccharide or any other organic or inorganic molecule, a killed or a live microorganism, such as bacteria, virus, fungus, phages, parasite, etc.

Notwithstanding the foregoing, the container may also contain cleaning products such as sanitization liquids or solutions, for example, benzyl alcohol, in order to decontaminate and clean the device before and after the injection sessions, e.g. the vaccination sessions.

The container receiving receptacle may contain different types of containers. Examples of containers that can be received into the container receiving receptacle are vials, flasks or the like which are well-known for those skilled in the art. Said containers for containing the medicinal products to be injected may be of different nature. For example they may be made of glass or plastic materials such as for example HDPE (High Density Polyethylene), LDPE (Low Density Polyethylene), PP (Polypropylene), PET (Polyethylene Terephthalate), etc.

The needle-free injection device further comprises a dispensing mechanism intended for causing the product in the container to be injected when the dispensing mechanism is operated. As used herein, injection involves administering said medicinal product to an animal through the skin (i.e. transdermal route), and specifically by intradermal route (when it is delivered below the dermis). Intramuscular or subcutaneous administration may be also possible depending on the injection parameters (injection pressure, injection volume, diameter of the nozzle) which are set in the device.

A RFID system associated with the above mentioned container receiving receptacle is also provided. The RFID system is capable of communicating with a RFID tag that is associated with the container. The RFID tag contains relevant information about the product contained in the container. Examples of said relevant information may be product manufacture date, expiry date, type of product, number of doses contained in the container, etc.

The RFID tag of the container can be uniquely identified by the RFID system. For this purpose, the RFID system sends an interrogating signal to the RFID tag via an antenna, and the RFID tag responds with its unique information. In some cases it may be useful that the injection device is provided with a display for at least displaying information to the user.

The RFID tag may be either active or passive. If an active RFID tag is provided, it contains its own power source such that it is capable of broadcasting with a read range of up to hundred meters. Its long read range makes the active RFID tag ideal for many industries where item location and traceability are important as it will be described further below. It may however be preferred that the RFID tag is passive so it does not have an own power source but it is powered by the electromagnetic energy transmitted from the RFID transceiver since radio waves are strong enough to power the RFID tag.

Administration of the product contained into the container can be allowed only under given conditions due to the communication between the RFID system and the RFID tag of the container. Said conditions may be predefined. For example, a predefined condition for allowing product administration may be that the product present in the container is the correct product to be injected to the animal.

As stated above, the RFID system includes an antenna for communication between the RFID system and the RFID tag of the container. The antenna is arranged such that it at least partially covers the RFID tag. As used herein, the fact that the antenna is arranged at least partially covering the RFID tag means that the antenna lies over at least one portion of the RFID tag such that communication between the RFID system and the RFID tag of the container is possible.

The RFID tag can be attached in one or more different positions in the container, such as the bottom of the container, the cap of the container, or any other suitable location of the container as long as the RFID tag can be in communication with the antenna, whether the antenna is at least partially covering the RFID tag or not.

It may be preferred that the antenna of the RFID system is flexible. In addition, a further preferred example of the antenna of the RFID system is curved in shape. In the example where a curved antenna is provided, the antenna may be arranged at least partially surrounding the RFID tag. More preferably, the RFID antenna may be arranged such that at least half of a length of the RFID tag is covered, or surrounded in the event that a curved antenna is provided. The provision of a curved antenna allows the RFID transceiver of the RFID system to be placed very close to the RFiD tag so that the RFID tag can be read correctly regardless the angular position of the container. Thus, even if the RFID tag of the container is placed in an angular position opposite the RFID system, the RFID tag can be read correctly across the container and thus across the product itself. This results in that the administration process can be carried out safely.

The RFID system may be configured for communicating bidirectionally with the RFID tag such that the RFID tag can be read and written by the RFID system. In some examples, the RFID system may comprise a RFID writer and a RFID reader. In this case, the RFID system is configured for communicating bidirectionally with the RFID tag such that the RFID tag can be read by the RFID reader and written by the RFID writer.

In any case, bidirectional communication allows information to be read from and written to the RFID tag of the container by the RFID system such that, for example, doses, time of the administration, product expiration date, product authentication, etc. can be easily and safely controlled. This further allows one to obtain a rough estimate of the remaining contents of product in the container to be injected. This results in one obtaining good traceability of product administered to a specific animal or batch of animals. Data collected from product injection sessions through the present needle-free injection device can then be processed by specific management applications such as for example in an animal farm.

The dispensing mechanism may be operated in cooperation with at least one sensor. Specifically, a contact sensor may be provided at the tip of the needle-free injection device. If product administration operation is allowed by the RFID system, a mechanical pressure on the tip of the injection device as it touches the animal's skin causes the dispensing mechanism to be triggered.

In some cases, it may advantageous that the RFID system is capable of adjusting an injection delay from the moment when the dispensing mechanism is triggered. This would result in that the administration of the medicinal product is delayed. Delay time depends on information that has been previously stored in the RFID tag of the container about the medicinal product to be administered. The information stored in the RFID tag based on which the injection may be delayed may for example correspond to the physic-chemical properties of the medicinal product, such as the viscosity, density, pH, etc. The injection delay may exist or not depending on the characteristics of the medicinal product. If injection delay is required, the injection delay may be fixed, e.g. according to a preset value, or it may be variable according to the requirements.

It is envisaged that the injection device may further include a product load inhibiting device. Said product load inhibiting device is intended for inhibiting the load of medicinal product. In one example, the product load inhibiting device may be configured for causing the load of the medicinal product to be inhibited from the container or vial into the injection device when a position of the container receiving receptacle has been detected to exceed a maximum inclination in space.

Such position of the container receiving receptacle exceeding a maximum inclination in space is considered not suitable for loading medicinal product. This ensures that the injection device is always loaded of medicinal product when the dispensing mechanism is triggered by the user. Triggering actions with no medicinal product, that is, dry shots, or triggering actions with incorrect doses of medicinal product are thus advantageously avoided. As a result, damages to internal parts, such as O-rings, in the injection device are also reduced or even eliminated.

The inhibiting device may comprise a tilt sensor device. The tilt sensor device may be connected to main circuit board. The main circuit board may be provided with a microcontroller capable of reading the positioning of the tilt sensor device. The tilt sensor device may include at least one of an accelerometer and a gyroscope. Other suitable sensor devices capable of performing the function of sensing the positioning or orientation in space of the injection device can be used. Depending on positioning or orientation in space of the injection device read by aid accelerometer and/or gyroscope when in use, the load of the medicinal product into the injection device is inhibited. As stated above, this will occur when the positioning or orientation in space of the injection device has been considered by the product load inhibiting device as not suitable. In that case, the user or operator may be warned through an audio or visual signal and/or through one or more messages on a display screen in the injection device itself and/or in a remote device.

In one example, said maximum inclination in space is defined by a tilt angle that is formed between a longitudinal axis of the container receiving receptacle and a vertical axis. The longitudinal axis of the container receiving receptacle may correspond to the longitudinal axis of the container or vial fitted therein. The vertical axis may be an axis forming an angle of at least substantially 90° with the horizontal, e.g. the ground. Other references for defining the above mentioned tilt angle may of course be used.

The maximum inclination in space of the container receiving receptacle beyond which the product load inhibiting device inhibits the load of the medicinal product corresponds to an inclination of a container or vial in the container receiving receptacle such that a volume of medicinal product inside the container is less than a predetermined volume, i.e., 0.2 ml (which is the delivery dose of the injection device). That is, when the injection device is positioned such that the vial or container fitted therein has a predetermined volume of medicinal product less than 0.2 ml, the product load inhibiting device inhibits the load of the medicinal product into the injection device.

The above predetermined volume corresponds to a preset dose of medicinal product and is configurable according to the requirements of the product load inhibiting device. Thus, the product load inhibition is software configurable according to said predetermined volume of medicinal product or according to the inclination in space of the injection device.

For most of 10-50 ml vials, the tilt angle for the above volume of medicinal product is within the range 10-60°, with 30-45° being preferred, and 45° most preferred. Those skilled in the art will readily recognize that the above inclinations include those whose angles are included within a cone where its height corresponds to the vertical axis and the generator line is or belongs to the longitudinal axis of the container receiving receptacle.

The container or vial has a mouth and a supply needle attached thereto. The supply needle has an outside portion that protrudes outwards the container mouth which is configured to be connected to delivery conduit. The supply needle also has an inner portion that is arranged inside the container. Said supply needle inner portion is and provided with a number of holes, such as for example four. Such holes may be preferably formed at a reduced distance from the mouth of the order of 5.0-6.0 mm, for example 5.2 mm. It is preferred that the holes of the needle have the same diameter and are formed each at the same distance from the mouth of the container.

The above configuration of holes, their positioning and number, together with the given values for the tilt angles, provide a good balance between the position of the injection device while ensuring a proper loading of the medicinal product into the injection device and thus an optimal operation mode of the injection device.

In addition, the product load inhibiting device allows the above mentioned holes of the supply needle inner portion to be always covered by medicinal product. Thus, when a tilt angle of the injection device has been detected such as at least one of said holes is not covered by medicinal product, the load is inhibited by the product load inhibiting device. This allows an optimal load of medicinal product into the injection device to be ensured.

In some examples, the RFID system may be further configured for communicating with a RFID tag external to the injection device. This allows total traceability of products administered to be recorded. Examples of external RFID tags may be animal identifiers. For this purpose, the RFID system could be operated at the same frequency as the external RFID tag.

Also in some examples, the RFID system may include a communications system for communicating with one or more external devices. The external device may be at least one selected from a PC, laptop, smartphone, tablet, etc. and even passive memories and the like. The communications system may also include a Bluetooth system such as a Bluetooth 4.0 system. A ModBus protocol may be implemented onto said Bluetooth communications system. The firmware of the device can be updated via the Bluetooth communications system or through a Modbus communications port. In addition, the Bluetooth communications system allows the device to be remotely set up and also to download operation logs that have been recorded. Operation logs may correspond, for example, to product administration operations carried out by the injection device. Advantageously, the operator has a greater control of the injection processes being carried out and the vaccine administered.

In some examples, the RFID system may include a NFC (Near Field Communication) system for retrieving an operating history in case of failure. The NFC is a specialized subset within the family of RFID technology. The NFC system is capable of communicating with an EEPROM memory in the device even if the device is broken or with no power.

A safe administration process is also provided since the medicinal product is only administered when the reading of the RFID tag in the container that contains the product is determined to be the correct one. The present needle-free injection device is a safe and advantageous tool useful to help in the prevention and control of disorders and diseases in animal health.

It is important to note that said reliable injection operation can be carried out regardless the positioning of the container into the device, that is, no matter how the container is placed within the container receiving receptacle of the device. In addition, the size of the container is not constrained and a wide variety of containers having different sizes, e.g. diameters, heights, can be used interchangeably with the present device. A further important advantage is that it has been found that a reliable operation of the present injection device is achieved regardless the arrangement of the RFID tag on the container.

However, the main advantage of the present needle-free injection device is that it provides wide product traceability and authentication due to the above described RFID system. The present needle-free injection device allows the user to retrieve data collected from product injection sessions and thus to obtain product authentication and traceability. Retrieved data can then be subsequently processed by specific applications developed for a specific management for example in an animal farm. Product traceability is of great importance when dealing with pharmaceutical products (i.e., vaccines, drugs, etc.) intended to prevent and/or treat diseases.

A system for managing the administration of medicinal products to animals is also disclosed herein. The managing system comprises the above described needle-free injection device and an external device configured to communicate with the injection device. Examples of external devices may be a PC, a laptop, a tablet, a smartphone, etc. Other external devices other than computer systems are not ruled out such as passive memories.

BRIEF DESCRIPTION OF THE DRAWINGS

Non-limiting examples of the present disclosure will be described in the following, with reference to the appended drawings, in which.

DETAILED DESCRIPTION OF EXAMPLES

Figure 1:
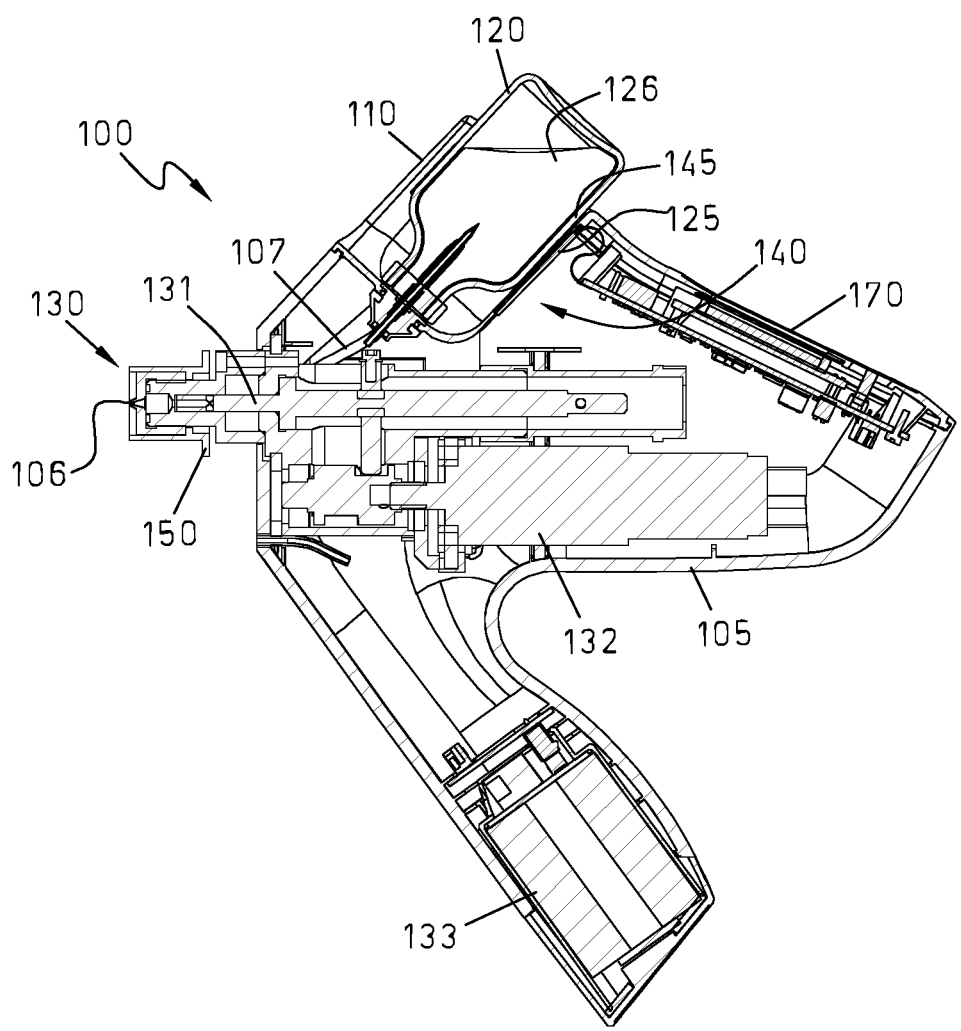
FIG. 1 is an elevational cutaway view along line AA in FIG. 2 of showing one possible example of the present needle-free injection device which is particularly suitable for administering a vaccine to an animal.
Figure 2:
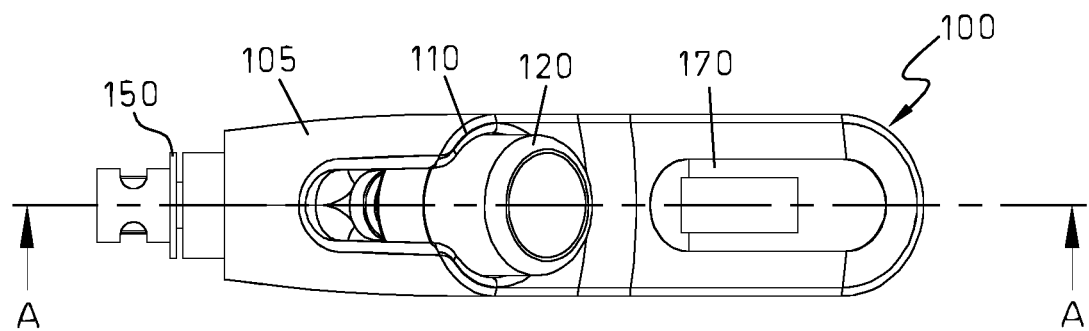
FIG. 2 is a top plan view of the device shown in FIG. 1.

The example of the present needle-free injection device shown in FIGS. 1 and 2 has been designated as a whole by reference numeral 100. The injection device 100 in the example shown is particularly suitable for administering a vaccine to an animal. Other applications of the injection device for administering other medicinal products are of course not ruled out.

The needle-free injection device 100 of the example shown comprises housing 105 where a number of device parts are received therein as it will be described below. In a top portion of the housing 105, a display 170 is provided. The display 170 is configured for displaying different information to the user, such as, for example, the number of doses of medicinal product 126 that have been injected, the number of doses left in the container 120 of the medicinal product 126, etc. It might be preferred that the display 170 is also configured to show different information regarding the number of doses in the container 120 remaining. It may be preferred that this information on the remaining dose is shown to the user every time the injection device 100 is turned off (remaining service).

The housing 105 of the injection device 100 further includes a container receiving receptacle 110 formed therein. The container receiving receptacle 110 in the example shown in FIG. 1 has a substantially cylindrical shape that is sized for receiving a great variety of different containers 120. In the example shown in the FIGS. 1 and 2, the container is a vial 120. The vial 120 is made for example of glass or plastic suitable for containing a vaccine product 126 to be administered to an animal. Different products other than vaccines, such as, for example cleaning liquids for decontaminating and cleaning the device 100 before and after being operated, may also be used.

A dispensing mechanism 130 is also received in the housing 105 of the needle-free injection device 100 shown in the figures. The dispensing mechanism 130 comprises a piston 131 movable within the housing 105 by means of a motor 132. The motor 132 is powered by a DC battery 133 that is also received in housing 105.

Displacement of the piston 131 within the housing 105 draws the medicinal product 126, in this example the vaccine, out of the vial 120 through a delivery conduit 107 leaving the injection device 100 through an outlet orifice 106. The vaccine 126 is thus supplied in the form of a fluid jet capable of piercing through the skin of the animal.

Associated with the container receiving receptacle 110 is a RFID system 140. The RFID system in this case is a transceiver 140 working at 13.56 MHz and coupled to the container receiving receptacle 110. The transceiver 140 is capable of communicating with a RFID tag 125 attached to the vial 120.

The RFID tag 125 of the vial 120 contains information that has been previously stored therein such as the type of vaccine, manufacture date, expiry date, number of doses contained in the vial 120, etc.

In the present example, the RFID tag 125 is passive so it does not have an own power source but it is powered by the electromagnetic energy transmitted from the RFID transceiver 140. Active RFID tags 125 coming with their own power source may be also used with the needle-free injection device 100.

The RFID system 140 further comprises a flexible curved antenna 145 for communicating with the RFID tag 125. In the preferred example shown in the FIGS. 1 and 2, the curved antenna 145 is arranged such that it surrounds at least half of a length of the RFID tag 125. As shown in FIG. 1, the antenna 145 is placed very close to the RFID tag 125 of the vial 120 by virtue of the curved shape of the antenna 145 and the curved shape of the RFID tag 125 attached to the vial 120. The curved shape of the antenna 145 results in an efficient reading of the RFID tag 125 by the RFID transceiver 140 regardless the angular position of the vial 120 within the container receiving receptacle 110 and the presence of liquid inside the vial 120. Therefore, the administration process can be thus carried out safely since the RFID tag 125 can be read by the RFID transceiver 140.

Through the flexible curved antenna 145, the RFID transceiver 140 is capable of communicating with the container RFID tag 125 for enabling the vaccine 126 contained within the vial 120 to be administered to the animal only under given predefined conditions, such as for example when it is detected that vaccine 126 is the correct or desired one to be injected.

When a cleaning solution is detected by the RFID system 140 inside the vial 120 placed in the container receiving receptacle 110 the needle-free device 100 is caused to be operated in a cleaning mode. In such cleaning mode, the cleaning solution is caused to be supplied without enough pressure, in a way that no injection can be performed.

Communications between the RFID transceiver 140 and the RFID tag 125 through the antenna 145 are bidirectionally. This involves that the RFID tag 125 can be read and written by the RFID transceiver 140. As a result, doses, time of administration, product expiration date, product authentication, etc. can be controlled and estimates of the remaining content of the medicinal product 126 in the vial 120 can be obtained. Therefore, product traceability is advantageously obtained.

A contact sensor 150 is provided at the tip of the injection device 100. The contact sensor 150 is connected to the dispensing mechanism 130 such that when the injection device 100 is pressed onto the animal's skin into which the vaccine 126 is to be administered, the dispensing mechanism 130 is actuated for performing product injection.

The RFID system 140 of the example is configured for communicating with other RFID tags (not shown) such an animal identifiers, external to the injection device 100, or with other external devices such as computing devices, e.g. laptops, tablets, smartphones and the like. Said external RFID tag allows administered product traceability to be obtained. Retrieved data can then be subsequently processed by specific applications developed for a specific management. The injection device 100 is thus capable of keeping logs of each injection process that has been carried out.

Other components in the injection device 100 of the example shown is a ModBus protocol implemented onto a Bluetooth 4.0 system through a RS485 port which allows, for example, the device firmware to be updated or remotely set up, a NFC (Near Field Communication) system for retrieving an operating history in case of failure, etc.

*In use, when the RFID system 140 detects that the vial 120 has no product therein, a "no product" warning message is shown in the display 170. If the RFID system 140 detects that the vial 120 has the correct product a "ready" message is shown in the display 170. Other messages can be displayed in the display 170 such as "loaded/unloaded" for showing whether a vial 120 is inserted into the vial receiving receptacle 110, "cleaning" when a cleaning operation is being performed, "menu" when browsing through various menu options, "purge" when a purge operation is being performed, for example when RFID system 140 detects that the current product 126 contained within the vial 120 is different from that of the last injection operation, "Bluetooth" for showing that the Bluetooth communication is enabled, "Modbus" for showing that the Modbus is connected and therefore manual controls are disabled, "normal operation" when the injection device 100 is in normal operation and many other messages relating to device status, such as battery status, different messages relating to device operation, etc.

Figure 3:
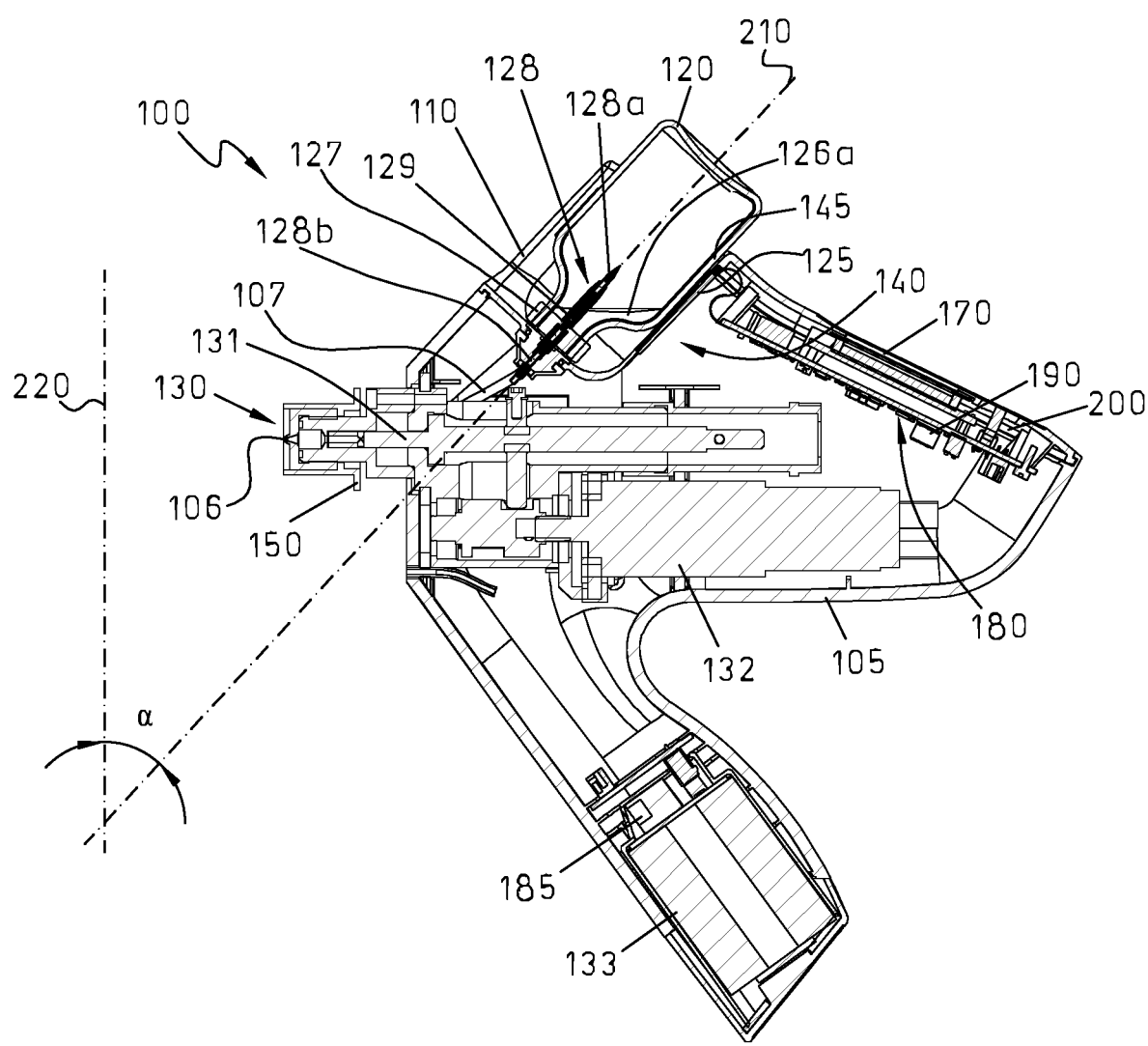
FIG. 3 is an elevational cutaway view according to FIG. 1 showing a further example of the present needle-free injection device provided with a product load inhibiting device.

In the specific example of the needle-free injection device 100 shown in FIG. 3 of the drawings, the injection device 100 is provided with a product load inhibiting device 180. The product load inhibiting device 180 is capable of inhibiting the load of medicinal product 126 from the container or vial 120 fitted in the container receiving receptacle 110 into the injection device 100.

Such product load inhibition is performed when a position of the container receiving receptacle 110 has been detected to exceed a maximum inclination α in space. It is to be noted that in such position exceeding the maximum inclination α, the product load inhibiting device 180 does not prevent the medicinal product 126 to be supplied or administered but it prevents the medicinal product 126 from being loaded into the injection device 100. The medicinal product 126 can be thus supplied or administered with the injection device 100 held at any desired position.

For this purpose, the inhibiting device 180 comprises a tilt sensor device 185 that is connected to the DC battery 133. A main circuit board 200 is provided having a small microcontroller 190 that is configured to read the positioning of the tilt sensor device 185 and thus that of the injection device 100.

In the non-limiting example shown in FIG. 3, the tilt sensor device includes an accelerometer 185. It is however understood that the tilt sensor device may include a gyroscope or both an accelerometer and a gyroscope or any other suitable device capable of sensing the positioning or orientation in the space of the injection device 100. In any case, the tilt sensor device 185 might in some cases include a number of accelerometers and/or gyroscopes and/or other devices, if required, connected to the DC battery 133 and the main circuit board 200.

When a positioning or orientation in the space of the injection device 100 is read by the accelerometer 185 such that the container 120 fitted therein has a volume 126*a* of medicinal product 126 less than a predetermined volume, for example 0.2 ml, the product load inhibiting device 180 inhibits the load of the medicinal product 126 into the injection device 100. In that case, the user or operator may be warned through an audio or visual signal and/or through one or more messages on the display screen 170 of the injection device 100 and/or in a remote device or unit (not shown).

In the example shown in FIG. 3, the inhibiting device 180 is configured such that the maximum inclination of the container receiving receptacle 110 in space is defined by tilt angle α. Tilt angle α is defined as an angle of inclination formed between a longitudinal axis 210 of the container receiving receptacle 110, that corresponds to the longitudinal axis 210 of the container 120, and a vertical axis 220 that is an axis forming an angle of at least substantially 90° with the horizontal, e.g. the ground. Thus, the possible orientations in space of the container receiving receptacle 110, and thus of the injection device 100, according to said tilt angle α, are included within a cone where the generator line corresponds to the above mentioned longitudinal axis 210 of the container receiving receptacle 110, and the cone axis or height corresponds to the above mentioned vertical axis 220. Said multiple possible orientations in space of the injection device 100 would correspond to the injection device 100 when turned forward or backward and/or right and left by the operator, for example.

Thus, when the needle-free injection device 100 is intended to be operated in a position out of said cone, the accelerometer 185 of the product load inhibiting device 180 prevents the product 126 from being loaded from the container or vial 120 into the injection device 100. In this example, the tilt angle α for the above volume 126*a* of medicinal product 126 inside the vial 120 lies within a range of 10-60°, with 30-45° being preferred, among which a tilt angle α of 45° is most preferred.

As shown in FIG. 3, the container or vial 120 has a mouth 127 and a supply needle 128 inserted therethrough. The supply needle 128 in the container or vial 120 has an outside portion 128*a* that is arranged protruding outwards therefrom configured to be connected to delivery conduit 107. The supply needle 128 also has an inner portion 128*b* that is arranged extending inside the container or vial 120. The inner portion 128*b* of the supply needle 128 is provided with four holes 129. Said holes 129 in the supply needle 128 are formed in this example at a distance of about 5.0-6.0 mm, for example 5.2 mm, from the mouth 127. Said supply needle holes 129 all have the same diameter and are formed each at the same above mentioned distance from the container mouth 127.

Although only a number of examples have been disclosed herein, other alternatives, modifications, uses and/or equivalents thereof are possible. Furthermore, all possible combinations of the examples that have been described are also covered. For example, the present injection device and managing system are not limited to the specifically disclosed applications and products. The RFID system may be any as long as it is capable of communicating with a RFID tag attached to a container for enabling the administration of a medicinal product only under given conditions. Thus, the scope of the present disclosure should not be limited by particular examples, but should be determined only by a fair reading of the claims that follow.

Reference signs related to drawings and placed in parentheses in a claim, are solely for attempting to increase the intelligibility of the claim, and shall not be construed as limiting the scope of the claim.

The invention claimed is:

1. A needle-free injection device for administering a medicinal product to an animal, the injection device comprising:

a container receiving receptacle configured for receiving a container containing the medicinal product;

a dispensing mechanism for dispensing the medicinal product;

a RFID system associated with the container receiving receptacle, capable of communicating with a RFID tag associated with the container, the RFID tag having information about the medicinal product present in the container, the RFID system being configured for enabling an administration of the medicinal product when, from the information read from the RFID tag, the medicinal product present in the container is identified as the correct product to be injected to the animal, wherein the RFID system comprises an antenna separate from the RFID tag and arranged at least partially covering the RFID tag and at least partially surrounding the RFID tag regardless of an angular position of the container in the container receiving receptacle, wherein the antenna is curved and flexible; and a contact sensor for operating the dispensing mechanism when the injection device is pressed onto an animal's skin, wherein the dispensing mechanism is associated with the contact sensor such that when a product administration operation is allowed by the RFID system, and simultaneously a mechanical pressure on the contact sensor as the injection device touches the animal's skin causes the dispensing mechanism to be triggered such that the medicinal product in the container is automatically injected into the animal.

2. The injection device of claim 1, wherein the antenna is arranged such that at least half of a length of the RFID tag is covered.

3. The injection device of claim 1, wherein an injection delay from a moment when the dispensing mechanism is triggered is set by the RFID system based on the information stored in the RFID tag about the medicinal product.

4. The injection device of claim 3, wherein the information stored in the RFID tag corresponds to a viscosity of the medicinal product.

5. The injection device of claim 1, wherein the injection device further includes a product load inhibiting device for inhibiting a load of the medicinal product.

6. The injection device of claim 5, wherein the product load inhibiting device is configured for causing the load of the medicinal product to be inhibited from the container into the injection device when a position of the container receiving receptacle exceeds a maximum inclination.

7. The injection device of claim 6, wherein the maximum inclination is defined by a tilt angle ($\alpha$) between a longitudinal axis of the container receiving receptacle and a vertical axis.

8. The injection device of claim 7, wherein the tilt angle ($\alpha$) corresponds to a volume of the medicinal product inside the container that is less than 0.2 ml.

9. The injection device of claim 7, wherein the tilt angle ($\alpha$) lies within a range of 10-60°.

10. The injection device of claim 5, wherein the product load inhibiting device comprises a tilt sensor device including at least one of an accelerometer and a gyroscope.

11. The injection device of claim 1, wherein the RFID system is configured for communicating bidirectionally with the RFID tag such that the RFID tag can be read and written by the RFID system.

12. The injection device of claim 1, wherein the RFID system is further configured for communicating with a second RFID tag external to the injection device.

13. The injection device of claim 1, wherein the RFID system includes a NFC (Near Field Communication) system for retrieving an operating history of the injection device, in case of failure.

14. The injection device of claim 1, wherein the RFID system includes a communications system for communicating with external devices.

15. The injection device of claim 14, wherein the communications system includes a Bluetooth system.

16. The injection device of claim 1, wherein the RFID system is configured for recording logs of product administration operations that are carried out by the injection device.

17. The injection device of claim 1, wherein the injection device is configured to inject the medicinal product through the animal's skin by transdermal, intradermal, subcutaneous or intramuscular route.

18. A system for managing an administration of medicinal products to an animal, comprising:

a needle-free injection device for administering at least one of the medicinal products to the animal, comprising a container receiving receptacle configured for receiving a container containing the medicinal product to be administered, a dispensing mechanism for dispensing the medicinal product; and a RFID system associated with the container receiving receptacle, capable of communicating with a RFID tag associated with the container, the RFID tag having information about the medicinal product present in the container, the RFID system being configured for enabling the administration of the medicinal product when, from the information read from the RFID tag, the medicinal product present in the container is identified as the correct product to be injected to the animal, wherein the RFID system comprises an antenna separate from the RFID tag and arranged at least partially covering the RFID tag and at least partially surrounding the RFID tag regardless of an angular position of the container in the container receiving receptacle, wherein the antenna is curved and flexible;

an external device configured to communicate with the injection device; and a contact sensor for operating the dispensing mechanism when the injection device is pressed onto an animal's skin, wherein the dispensing mechanism is associated with the contact sensor such that when a product administration operation is allowed by the RFID system, and simultaneously a mechanical pressure on the contact sensor as the injection device touches the animal's skin causes the dispensing mechanism to be triggered such that the medicinal product in the container is automatically injected into the animal.

19. The system of claim 18, wherein the external device is one of a PC, laptop, smartphone, or a tablet.

* * * * *